US012575861B2

(12) United States Patent
     Faulhaber

(10) Patent No.: US 12,575,861 B2
(45) Date of Patent: Mar. 17, 2026

(54) LOCKING COUPLER DEVICE FOR SPINE ALIGNMENT

(71) Applicant: GLOBUS MEDICAL, INC., Audubon, PA (US)

(72) Inventor: Kurt Faulhaber, Cape Coral, FL (US)

(73) Assignee: Globus Medical, Inc., Audubon, PA (US)

( * ) Notice: Subject to any disclaimer, the term of this patent is extended or adjusted under 35 U.S.C. 154(b) by 1 day.

(21) Appl. No.: 18/661,983

(22) Filed: May 13, 2024

(65) Prior Publication Data

US 2024/0293155 A1    Sep. 5, 2024

Related U.S. Application Data

(63) Continuation of application No. 17/406,337, filed on Aug. 19, 2021, now Pat. No. 11,986,220, which is a continuation of application No. 16/394,437, filed on Apr. 25, 2019, now Pat. No. 11,103,284.

(51) Int. Cl.
*A61B 17/70* (2006.01)
*A61B 17/68* (2006.01)

(52) U.S. Cl.
CPC .... *A61B 17/7032* (2013.01); *A61B 2017/681* (2013.01)

(58) Field of Classification Search
CPC ............ A61B 17/7032; A61B 17/7049; A61B 17/7074; A61B 17/7076; A61B 17/7077; A61B 17/7083; A61B 17/7086; A61B 17/7025

USPC ................................................ 606/277, 279
See application file for complete search history.

(56) References Cited

U.S. PATENT DOCUMENTS

| | | | | |
|---|---|---|---|---|
| 11,103,284 | B2 * | 8/2021 | Faulhaber .......... | A61B 17/7079 |
| 11,771,477 | B2 * | 10/2023 | Smith .................... | A61B 17/70 |
| | | | | 606/279 |
| 11,986,220 | B2 * | 5/2024 | Faulhaber .......... | A61B 17/7032 |
| 12,070,252 | B2 * | 8/2024 | Hammann ......... | A61B 17/7079 |
| 12,089,881 | B2 * | 9/2024 | Olea .................. | A61B 17/7001 |
| 2014/0039567 | A1 * | 2/2014 | Hoefer ............... | A61B 17/7082 |
| | | | | 606/86 A |

* cited by examiner

*Primary Examiner* — Eduardo C Robert
*Assistant Examiner* — Christina Negrellirodriguez

(57) ABSTRACT

Embodiments are directed to an apparatus for aligning vertebrae of a curved spine that may include a coupler having a longitudinal axis, a proximal end, and a distal end, wherein the proximal end comprises first threads, wherein the distal end comprises a mating surface for disposition around a rod attached to a spinal column, and wherein the coupler applies a compressive clamping force to the rod. The apparatus further may include a nut having second threads corresponding to the first threads, wherein the nut is attachable to the coupler proximal end. The apparatus further may include a driver disposable at least partially around the coupler, wherein the driver applies a clamping force to the coupler, and wherein the nut applies a linear force to the driver when tightened.

10 Claims, 7 Drawing Sheets

LOCKING COUPLER DEVICE FOR SPINE ALIGNMENT

CROSS-REFERENCE TO RELATED APPLICATIONS

The present application is a continuation of U.S. patent application Ser. No. 17/406,337, filed on Aug. 19, 2021, which is a continuation of U.S. patent application Ser. No. 16/394,437, filed on Apr. 25, 2019, all of which are incorporated herein in their entirety by reference.

BACKGROUND

A common medical problem is a curved spine caused by dislocated vertebra. A curved spine can cause pain, suffering, restricted motion, and a loss of quality of life for a person. A curved spine can be caused by a congenital defect, an injury or accident, or by gradual decay of supporting bone structure over time. In some cases, alleviating the symptoms of a curved spine does not require surgery. However, surgery is often required to correct the alignment of vertebrae and to relieve the pain. Surgery may involve fusing two adjacent vertebrae together or other invasive procedures. However, patients with fused spines often experience limited motion and, in some cases, a stooped appearance. What is needed are improved apparatus to counteract the curved spine in an effort to reduce the effects and to relieve a patient's limited motion, pain, and suffering.

SUMMARY

In an exemplary embodiment, the present disclosure provides an apparatus for aligning vertebrae of a curved spine. The apparatus may include a coupler having a longitudinal axis, a proximal end, and a distal end, wherein the proximal end comprises first threads, wherein the distal end comprises a mating surface for disposition around a rod attached to a spinal column, and wherein the coupler applies a compressive clamping force to the rod. The apparatus may further include a nut having second threads corresponding to the first threads, wherein the nut is attachable to the coupler proximal end. The apparatus may further include a driver disposable at least partially around the coupler, wherein the driver applies a clamping force to the coupler, and wherein the nut applies a linear force to the driver when tightened.

In another exemplary embodiment, the present disclosure provides a system for aligning vertebrae of a curved spine. The system may include a pair of locking coupler assemblies. Each of the locking coupler assemblies may include a coupler having a longitudinal axis, a proximal end, and a distal end, wherein the proximal end comprises first threads, wherein the distal end comprises a mating surface for disposition around a rod attached to a spinal column, and wherein the coupler applies a compressive clamping force to the rod. Each of the locking coupler assemblies may further include a nut having second threads corresponding to the first threads, wherein the nut is attachable to the coupler proximal end. Each of the locking coupler assemblies may further include a driver disposable at least partially around the coupler, wherein the driver applies a clamping force to the coupler, and wherein the nut applies a linear force to the driver when tightened. The system may further include a distractor tool attachable to the locking coupler assemblies and operable to move apart the locking coupler assemblies from one another.

In yet another embodiment, the present disclosure provides a method for aligning vertebrae of a curved spine. The method may include tightening a first locking coupler assembly onto a rod, wherein the rod is attached to a spinal column by way of bone fasteners distributed along the spinal column. The method may further include tightening a second locking coupler assembly onto the rod. The method may further include forcing the first locking coupler assembly to move along the rod way from the second locking coupler assembly such that one or more of the bone fasteners are forced more into alignment with an adjacent one of the bone fasteners.

BRIEF DESCRIPTION OF THE DRAWINGS

These drawings illustrate certain aspects of some examples of the present invention, and should not be used to limit or define the invention, wherein.

DETAILED DESCRIPTION

Embodiments are directed to an apparatus for aligning vertebrae of a curved spine. More particularly, embodiments may include a locking coupler assembly that may be used in aligning vertebrae of a covered spine. In operation, a pair of locking coupler assemblies may be attached a rod at adjacent segments. In at least one embodiment, the rod may be placed but not fixed to a pedicle screw. The locking coupler assemblies may then be moved apart with at least one of the locking coupler assemblies moving along the rod toward the adjacent segment. This should place the adjacent segments more in line. After which, the rod may be fixed to the pedicle screw, and the process may be repeated at one or more additional levels in the vertebral column.

Embodiments of the locking coupler assembly may include a coupler, a driver, and a nut. In some embodiments, the coupler may have a longitudinal axis, a proximal end, and a distal end, where the proximal end includes first threads, the distal end has a mating surface for disposition around a rod fixably attached to a vertebra, and the coupler applies a compressive clamping force to the rod. In some embodiments, the nut may include second threads corresponding to the first threads of the coupler, where the nut is attachable to the proximal end of the coupler. In some embodiments, the driver may be disposable at least partially around the coupler, where the driver can apply a clamping force to the coupler, and where the nut applies a linear force to the driver when tightened.

Figure 1:
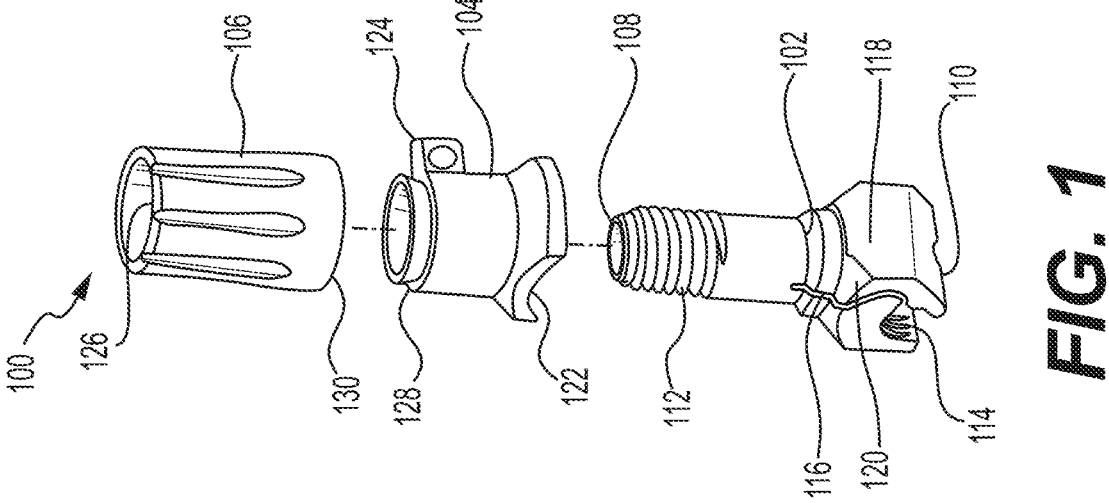
FIG. 1 illustrates components of a locking coupler assembly.

FIG. 1 illustrates components of a locking coupler assembly 100 in accordance with example embodiments. As illustrated, the locking coupler assembly may include a coupler 102 with a proximate end 108 and a distal end 110. According to some embodiments, the coupler 102 may be a hollow cylinder-shaped structure with a set of first threads 112 at the proximate end 108 and a mating surface 114 at the distal end 110. In the illustrated embodiment, the distal end 110 also includes a split seam 116, which may extend along a longitudinal axis of the coupler 102. The split seam 116 may extend a distance from the distal end 110 towards the proximate end 108 and may define a moveable and spring-like extension arm 118. The extension arm 118 may be configured to flex radially towards the longitudinal axis of the coupler 102. According to some embodiments, the extension arm 118 may include portions of the mating surface 114. In some embodiments, the mating surface 114 may have a smooth surface (e.g., smooth finish 700 on FIG. 7) while in other embodiments, the mating surface 114 is made of a textures or serrated surface (e.g., textured finish 800 on FIG. 8) to aid in gripping a rod or other object positioned within the distal end 110 of the coupler 102. In some embodiments, the coupler 102 also may include an angled shoulder 120 that can be located at or near a central region of the coupler 102. The angled shoulder 120 may be positioned along the coupler 102 so that the split seam 116 extends a distance further towards the proximate end 108 than the angled shoulder 120. In some embodiments, the angled shoulder 120 may be positioned along the coupler 102 such that portions of the angled shoulder 120 are located on the coupler 102 itself and form a portion of the extension arm 118, thus providing a location where force can be applied to the coupler 102 to make the extension arm 118 flex relative to the coupler 102. In operation, when a longitudinal force is applied to the angled shoulder 120, the extension arm 118 is pushed inwards towards the center or longitudinal axis of the coupler 102 and compresses the mating surface 114 to form a clamping effect around a rod, in accordance with example embodiments. According to some embodiments, the locking coupler assembly 100 is included of at least one of stainless steel, titanium, nitinol, nylon, phenolic, resin, or composite material.

At least one embodiment of the locking coupler assembly 100 also includes a driver 104. In some embodiments, the driver 104 may be made of a hollow cylinder-like structure having a forcing surface 122 and an attachment lug 124. The forcing surface 122 may be angled to correspond to the angled shoulder 120 of the coupler 102. According to some embodiments, the forcing surface 122 has approximately the same angle as the angled shoulder 120. In other embodiments, the forcing surface 122 is orthogonal to the angled shoulder 120. In accordance with example embodiments, the driver 102 is configured to slide over the proximate end 108 of the coupler 102 and over the first threads 112 of the coupler 102 to allow the forcing surface 122 to couple with the angled shoulder 120 of the coupler 102. By way of example, when the driver 104 and thus the forcing surface 122, is driven towards the distal end 110 of the coupler 102, the forcing surface 122 should apply a longitudinal force to the angled shoulder 120 of the coupler 102, for example, to compress the extension arm 118 inwards. By way of further example, the resultant movement of the extension arm 118 should tighten the coupler 102 against an object, such as a rod, positioned in proximity to the mating surface 114. The attachment lug 124 may be configured to engage with an installation tool (e.g., distractor tool 900 on FIG. 9). The driver 104 may also include a loading surface 128 that can be configured to receive a longitudinal force and transfer the force to the forcing surface 122.

At least one embodiment of the locking coupler assembly 100 also includes a nut 106. In some embodiments, the nut 106 and the driver 104 may be separate components. In other embodiments (not shown), the nut 106 and the driver 104 may be integrally formed. As illustrated, the nut 106 may have a set of second threads 126 that correspond to the set of first threads 112 of the coupler 102. According to some embodiments, the second threads are positioned on an interior surface of the nut 106 corresponding to the first threads 112 positioned on an exterior surface of the coupler 102. In other embodiments, the first threads 122 are internal threads and the second threads 126 are external threads. In operation, for example, when the nut 106 is tightened against the coupler 102 using the second threads 126 engaging the first threads 112, the nut 106 should apply a longitudinal force to the driver 104 by applying force from the driving surface 130 of the nut 106 to the loading surface 128 of the driver 104. The driver 104 then should apply a longitudinal force via the forcing surface 122 to the angled shoulder 120 of the coupler 102. By way of example, applying the longitudinal force to the angled shoulder 120 should compress the extension arm 118 and collapses the split seam 116, thus tightening the coupler's 102 distal end 110 against a rod or other object located in proximity to the mating surface 114.

Figure 2:
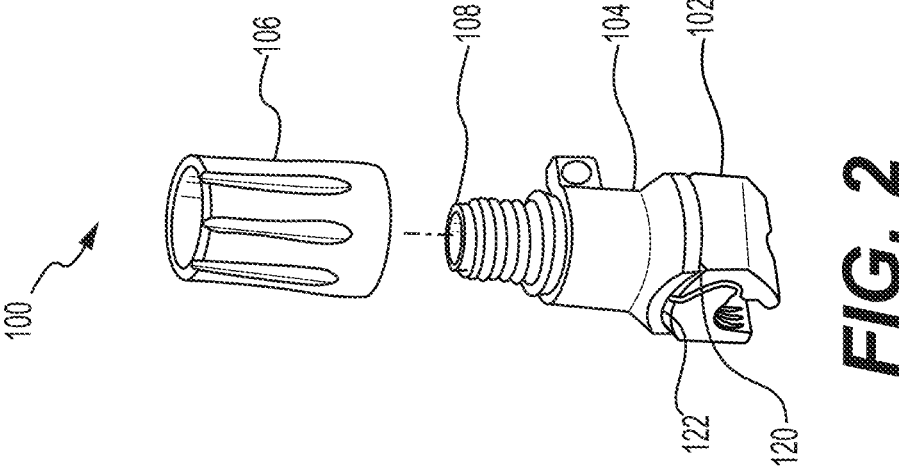
FIG. 2 illustrates a locking coupler assembly partially assembled.

FIG. 2 illustrates a locking coupler assembly 100 partially assembled, in accordance with example embodiments, with the driver 104 positioned over the proximate end 108 of the coupler 102 and the forcing surface 122 of the driver 104 in proximity to the angled shoulder 120 of the coupler 102. The nut 106 is shown a distance away from the locking coupler assembly 100.

Figure 3:
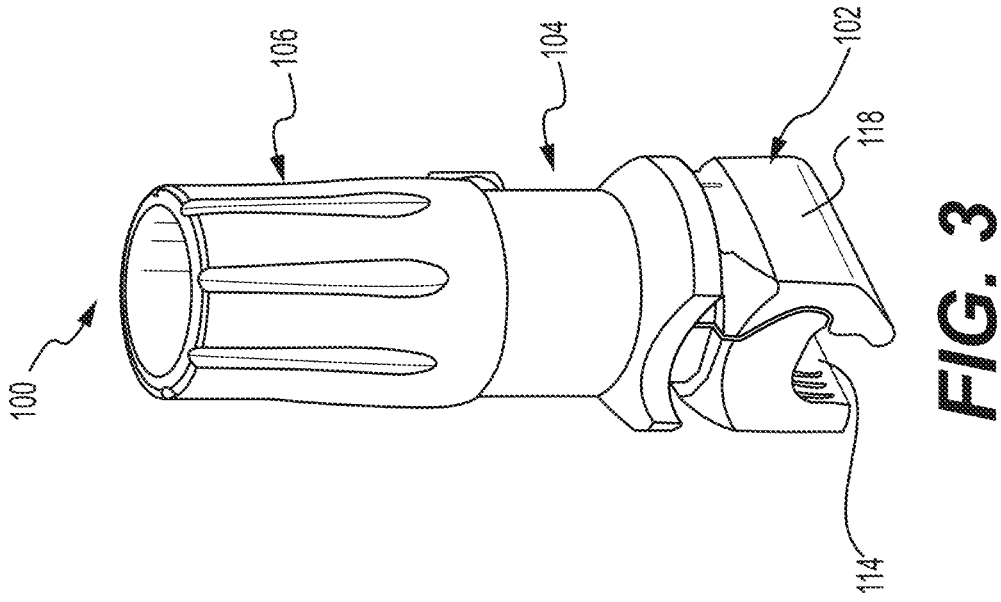
FIG. 3 illustrates a locking coupler assembly in an untightened state.

FIG. 3 illustrates a locking coupler assembly 100 in an untightened state, in accordance with example embodiments. As illustrated, the nut 106 is loosely threaded to the coupler 102 and the driver 104 is not under force. In this position, the extension arm 118 is not driven inwards by force, and an object in proximity to the mating surface 114 is not fixably attached to the locking coupler assembly 100. In the unlocked state, the locking coupler assembly 100 can be positioned along the rod and placed in a location and orientation prior to tightening the nut 106 to form a fixed alignment.

Figure 4:
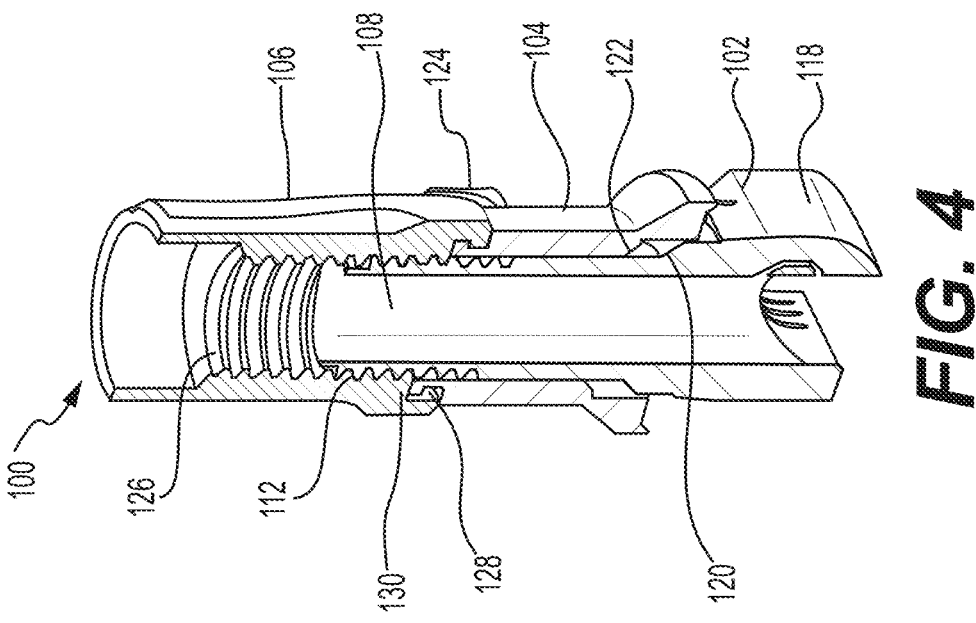
FIG. 4 illustrates a cutaway view of a locking coupler assembly in an untightened state.

FIG. 4 illustrates a cutaway view of a locking coupler assembly 100 in an untightened state, in accordance with example embodiments. As illustrated, the forcing surface 122 of the driver 104 is not in contact with the angled shoulder 120 of the coupler 102, thus no force is applied to the extension arm 118. Also shown is the arrangement of the first threads 112 of the coupler 102 with the second threads 126 of the nut 106, for example, when the nut 106 is partially threaded onto the proximate end 108 of the coupler 102. Also shown is the arrangement of the driving surface 130 of the nut 106 in contact with the loading surface 128 of the driver 104. In this arrangement, as the nut 106 is turned, additional force is applied to the driver 104 through the movement of the driving surface 130 pushing on the loading surface 128. This causes the forcing surface 122 of the driver to move towards the angled shoulder 120 of the coupler 102.

Figure 5:
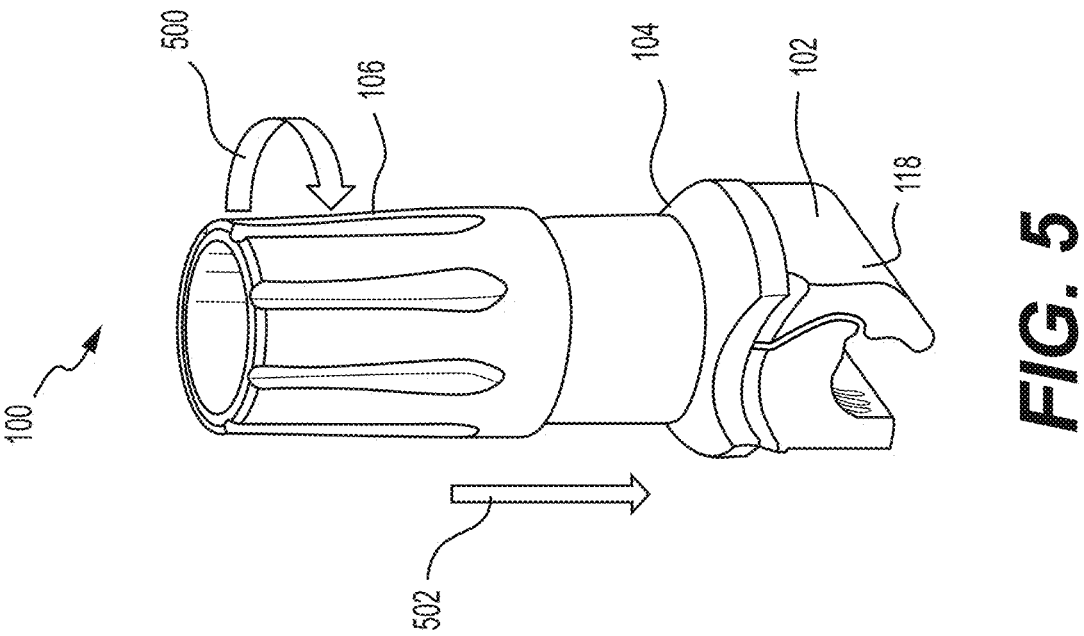
FIG. 5 illustrates a locking coupler assembly in a tightened state.

FIG. 5 illustrates a locking coupler assembly 100 in a tightened state in accordance with example embodiments. As illustrated, the nut 106 may be tightened against the coupler 102 and forcing the driver 104 to compress the extension arm 118. According to some embodiments, the nut 106 may be rotated, for example, in the direction shown by arrow 500 to tighten the nut 106 onto the coupler 102. In some embodiments, the direction may be clockwise. In other embodiments (not shown), the direction may be counter-clockwise. The nut 106 may be loosen when rotated in the opposite direction. As the nut 106 is rotated in the direction 500 and tightens onto the coupler 102, in accordance with example embodiments, the nut 106 should apply a force in the direction shown by arrow 502 to the driver 104 that drives the driver 104 down the coupler 102 compressing the extension arm 118.

Figure 6:
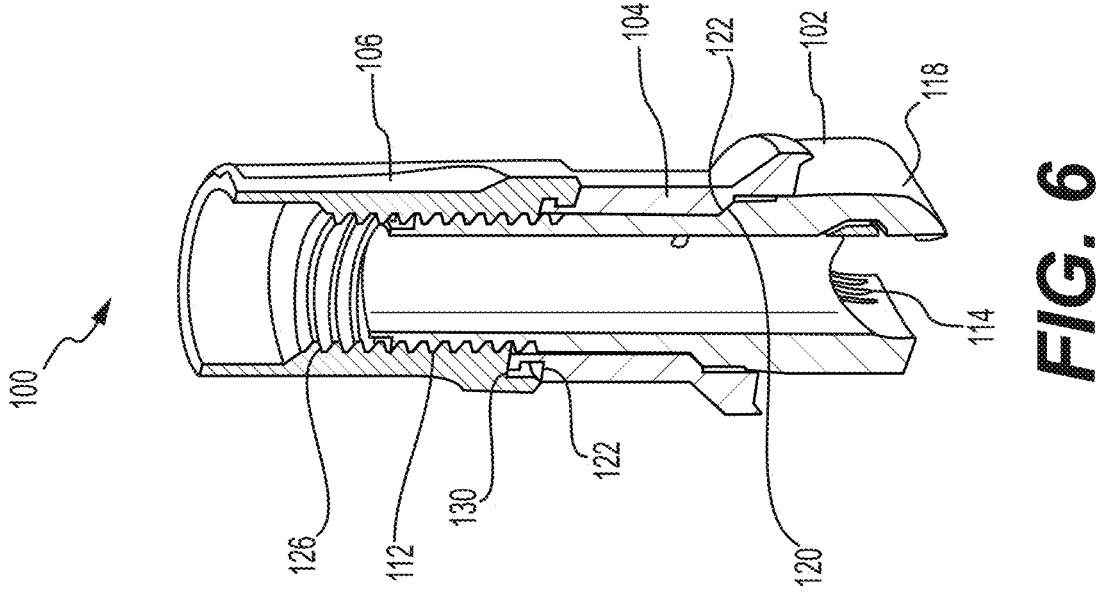
FIG. 6 illustrates a cutaway view of a locking coupler assembly in a tightened state.

FIG. 6 illustrates a cutaway view of a locking coupler assembly 100 in a tightened state, in accordance with example embodiments. As illustrated, the forcing surface 122 of the driver 104 may be in full contact with the angled shoulder 120 of the coupler 102. Thus positioned, the extension arm 118 may be pushed towards the longitudinal axis of the coupler 102 and compresses an object, such as a rod, that is located adjacent to the mating surface 114.

Operation of locking coupler assembly 100 will now be described with respect to FIGS. 3-6, in accordance with example embodiments. In operation, the coupler 102 of the locking coupler assembly 100 may be placed in position around an object (not shown), such as a rod, with the locking coupler assembly 100 in an untightened state, as shown on FIGS. 3 and 4. In the untightened state, the locking coupler assembly 100 is not tightened and the rod can be inserted adjacent to the mating surface 114 without difficulty. Once the rod is in position, the nut 106 may be rotated, as shown on FIGS. 5 and 6, and tightened to engage the driver 104. As the nut 106 is tightened, the driver 104 should be forced to drive against the angled shoulder 120 of the coupler 102 and thus begins to force the extension arm 118 inwards towards the rod. Additional tightening of the nut 106 should increases the force to the driver 104 and the extension arm 118 until a medical professional determines that sufficient force has been applied to fasten the locking coupler assembly 100 in place on the rod. According to some embodiments, the nut 106 incudes a locking mechanism for preventing the nut 106 from being loosened inadvertently. The locking mechanism can be at least one of a lock ring, a lock washer, a ratcheting surface, a lock nut, an adhesive, or the like. According to some embodiments, an installation/removal tool (not shown) is used to tighten the nut 106. By way of example, the installation/removal tool can be a screwdriver, nut driver, wrench, or the like.

Figure 7:
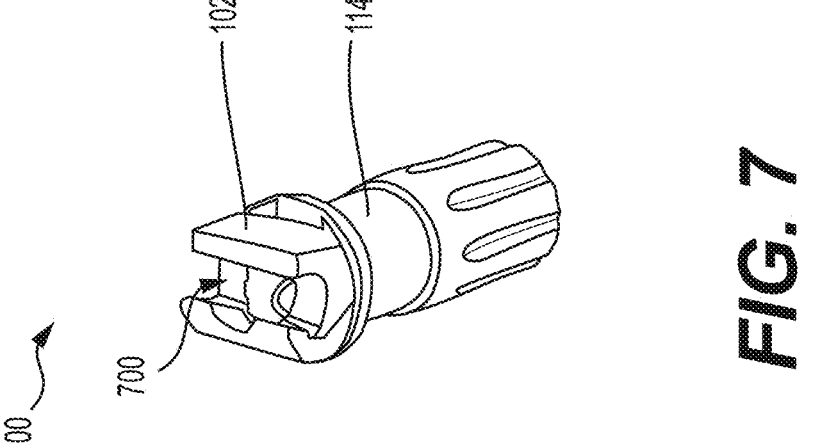
FIG. 7 illustrates a locking coupler assembly having a smooth mating surface.

FIG. 7 illustrates a locking coupler assembly 100, in accordance with example embodiments. As illustrated, the mating surface 114 of the coupler 102 may have a smooth finish 700. According to some embodiments, the smooth finish 800 provides sufficient clamping force to an object, such as a rod, as to hinder movement or rotation of the locking coupler assembly 100 when it is fixably attached to the object. However, the smooth finish 700 may still allow the rod (or other object) to slide in the coupler 102.

Figure 8:
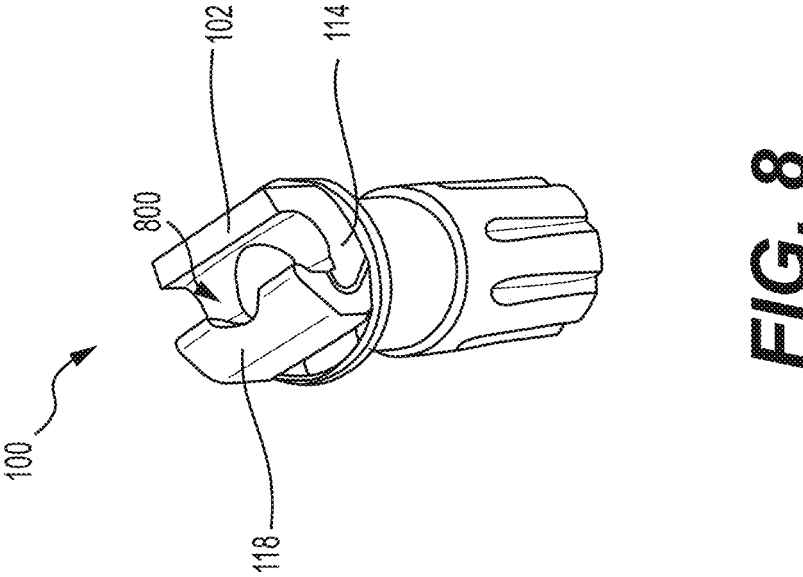
FIG. 8 illustrates a locking coupler assembly having a textured mating surface.

FIG. 8 illustrates another embodiment of a locking coupler assembly 100. As illustrated, the mating surface 114 of the coupler 102 may have a textured finish 800. According to some embodiments, the textured finish 800 is made at least one of ridges, abrasions, serrations, divots, or the like to improve the clamping force applied by the extension arm 118 when the locking coupler assembly 100 is tightened around an object, such as a rod.

Figure 10:
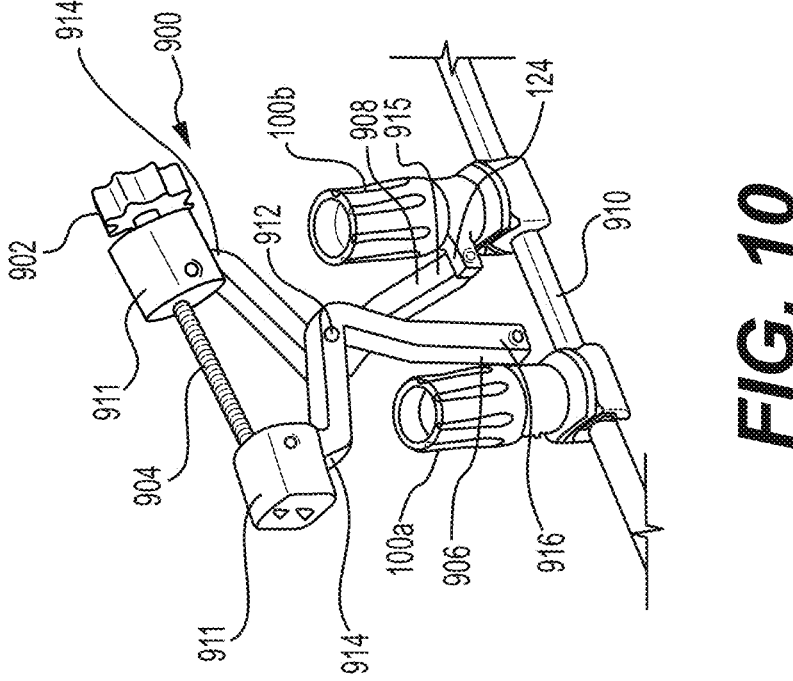
FIGS. 9 and 10 illustrate a distractor tool, a rod, and two locking coupler assemblies in unlocked and locked states.
Figure 9:
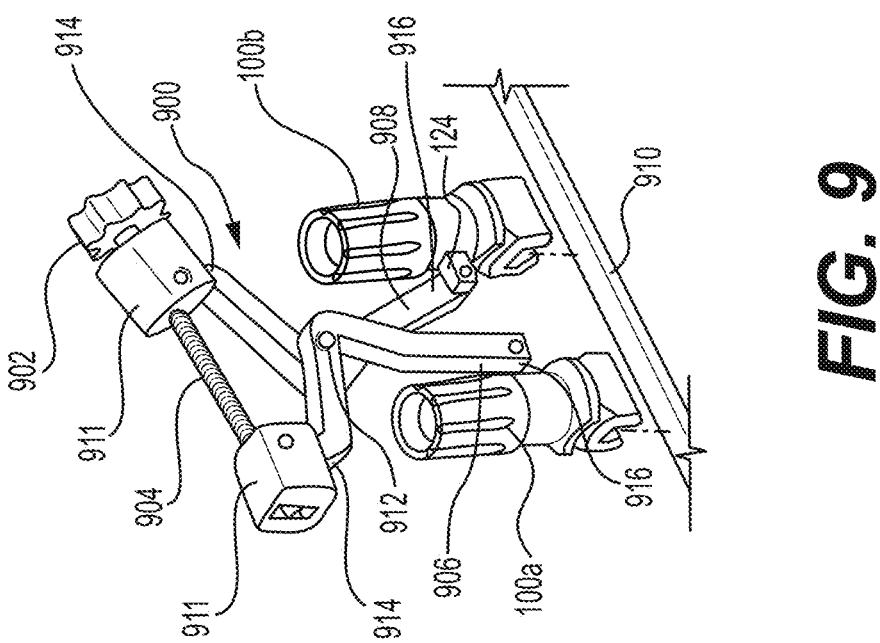
Figure 12:
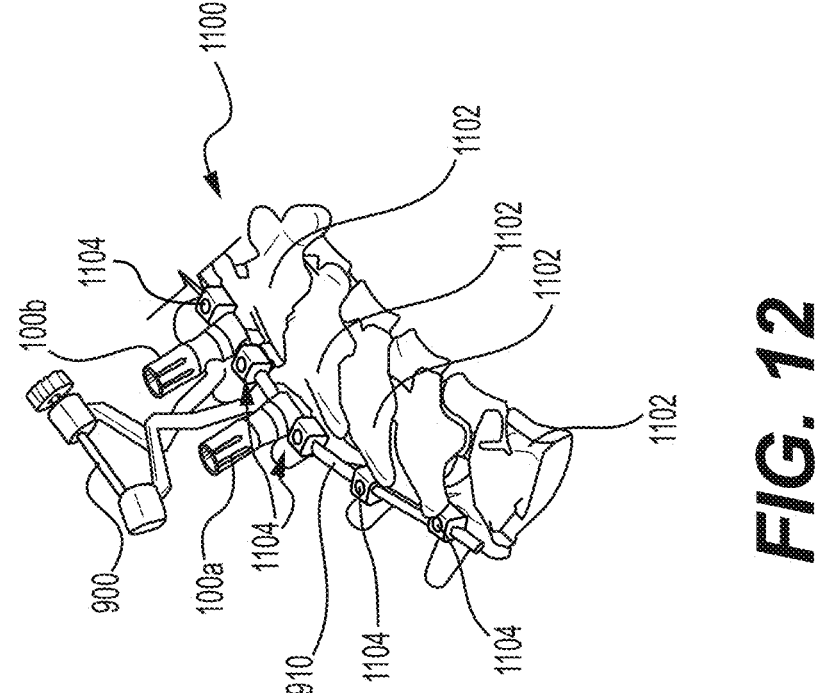
FIGS. 11 and 12 illustrate a rod affixed to vertebrae with two locking coupler assemblies being aligned by a distractor tool.

FIGS. 9 and 10 illustrate use of locking coupler assemblies 100a and 100b with a distractor tool 900, in accordance with example embodiments. The distractor tool 900 may be coupled to the locking coupler assemblies 100a and 100b, referred to individually as first locking coupler assembly 100a and second locking coupler assembly 100b. As illustrated, the distractor tool 900 may include an adjustment knob 902, a screw 904, a first arm 906, a second arm 908, and pivoting blocks 911. As illustrated, the screw 904 may extend from the adjustment knob 902 through the pivoting blocks 911. While not shown, the pivoting blocks 911 may have a threaded through passage that engages the screw 904. Alternatively, a ratcheting mechanism may be used in place of threading. The first arm 906 and the second arm 908 may each have a proximal end 914 and a distal end 916. The first arm 906 and the second arm 908 may also be coupled at pivot 912. Accordingly, when proximal ends 914 of the first arm 906 and second arm 908 are moved together, the distal ends of the first arm 906 and the second arm 908 are moved apart. The proximal ends 914 may be secured to the pivoting blocks 911. The distal ends 916 may be secured to the locking coupled assemblies 100a and 100b. As illustrated, the first arm 906 and the second arm 908 may be attached to the locking coupler assemblies 100a and 100b by connecting to the attachment lug 124 of FIG. 1. For example, the first arm 906 may be coupled to the first locking coupler assembly 100a, and the second arm 908 may be coupled to the second locking coupler assembly 100b. In operation, the adjustment knob 902 may be rotate to pull the pivoting blocks 110 and in turn the proximal ends 914 of the first arm 906 and second arm 908 closer to one another. By moving the proximal ends 914 closer to another, the distal ends 916 and, in turn, the locking coupler assemblies 100a and 100b may be moved apart. In operation, the first arm 906 and the second arm 908 may pivot with respect to the pivoting blocks 911, for example, to maintain the locking coupler assemblies 100a and 100b parallel when moved apart from one another.

Rod 910 is also illustrated on FIGS. 9 and 10. While not shown, the rod 910 may be is affixed to the vertebrae of a spinal column using screws or other fasteners to limit curvature and improve bone alignment. According to some embodiments, the rod 910 is fixably attached to vertebrae of the spine during a surgical procedure. As shown on FIG. 9, the locking coupler assemblies 100a and 100b may be placed onto the rod 910 in an untightened state in accordance with example embodiments. FIG. 10 illustrates the locking coupler assemblies 110a and 100b attached to the rod 910 after tightening in accordance with example embodiments. As a result, the distraction tool 900 may be used to push apart (or pull together) the two locking coupler assemblies 100 and 100b. For example, the two locking coupler assemblies 100a and 100b may be pushed apart or pulled together along the rod 910 depending on whether the adjustment knob 904 of the distractor tool 900 is turned clockwise or counter-clockwise.

Figure 11:
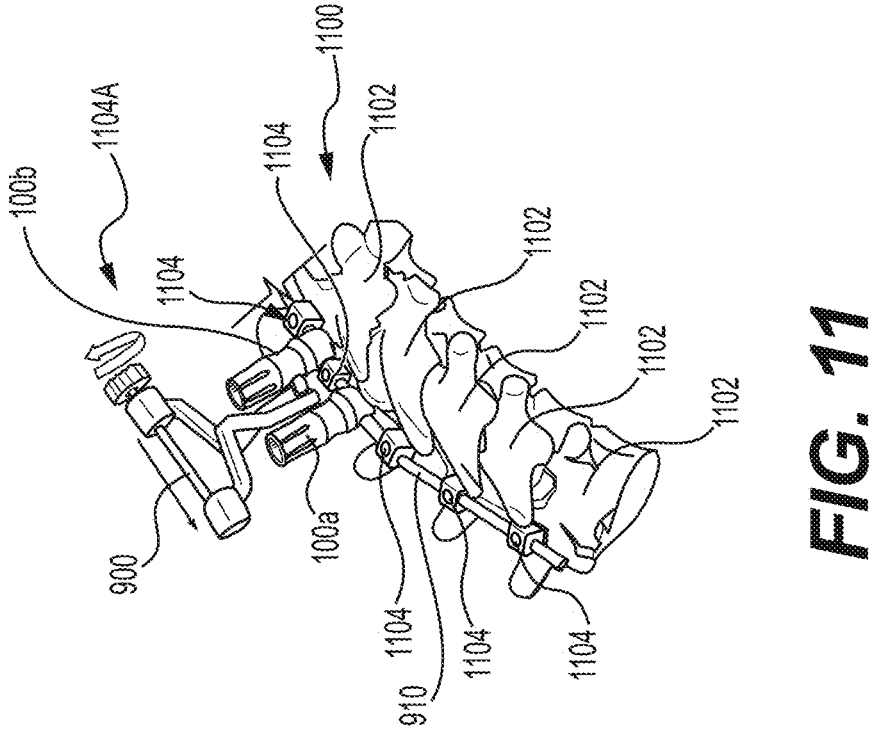
Figure 14:
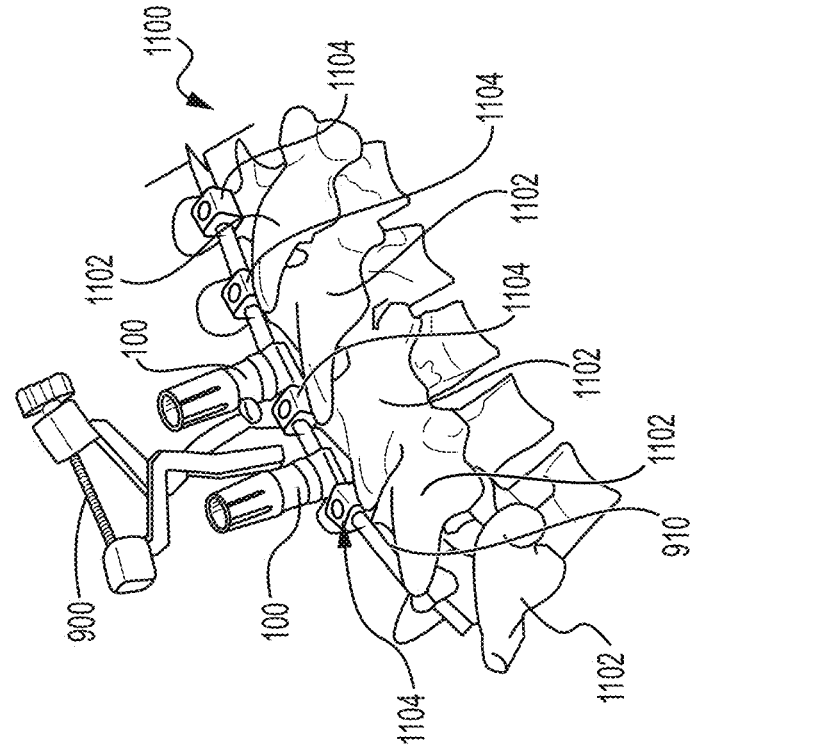
FIGS. 13 and 14 illustrate the rod affixed to vertebrae of FIGS. 11 and 12 with two locking coupler assemblies being aligned by a distractor tool at a different level.
Figure 13:

Operation of locking coupler assemblies 100a and 100b in a spinal procedure will now be described in more detail with respect to FIGS. 11-14. As illustrated, rod 910 may be arranged in a segment of spinal column 1100. Bone fasteners 1104 distributed along the spinal column 1100 in corresponding vertebrae 1102. Suitable bone fasteners 1104 may include, but are not limited to, pedicle screws or single or double vertebral hooks with a fixation head for the rod 910. The rod 910 may be arranged in the spinal column 1100 to link the fasteners together. However, the rod 910 may not yet be fixed to one or more of the bone fasteners 1104 in a locked position. With reference to FIG. 11, the locking coupler assemblies 100*a*, 100*b* may be installed onto the rod 900, for example, as previously described. For example, the locking coupler assemblies 100*a*, 100*b* may be clamped onto a segment of the rod 910. In some embodiments, the first locking coupler assembly 100*a* may have a smooth finish 700 (e.g., shown on FIG. 7), thus allowing movement on the rod 910 when clamped thereon while the second locking coupler assembly 100*b* may have a textured finish 800 (e.g., shown on FIG. 8), thus restricting movement along the rod 910 when clamped thereon. Once installed on the rod 910, the distractor tool 900 may be operated to force the locking coupler assemblies 100*a* and 100*b* apart. For example, the first locking coupler assembly 100 may be moved along the rod 910, as shown on FIG. 12), while the second locking coupler assembly 100*b* remains stationary. As the locking coupler assemblies 100*a* and 100*b* are forced apart, movement of the corresponding bone fasteners 1104, and, thus, the vertebrae 1102 is induced, forcing adjacent vertebrae more into alignment by parallelism. When the first locking coupler assembly 100*a* has been moved to a desired position along the rod 910, embodiments may then include locking the rod 910 in the bone fasteners 110 in the segment of the rod 910 in which the locking coupler assemblies 100*a*, 100*b* were applied. The locking coupler assemblies 110*a* and 100*b* may then be loosened and removed from the rod 910. As illustrated by FIG. 13, embodiments may include attaching the locking coupler assemblies 100*a* and 100*b* to the rod 910 at another position in the spinal column 1100. The distractor tool 900 may then be operated to force the locking coupler assemblies 100*a* and 100*b* apart, as shown in FIG. 14. When the first locking coupler assembly 100*a* has been moved to a desired position along the rod 910, embodiments may then include locking the rod 910 in the bone fasteners 110 in the additional segment of the rod 910 in which the locking coupler assemblies 100*a*, 100*b* were moved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of aligning vertebrae of a curved spine comprised of:
   providing a locking rod coupler including a locking coupler having a mating surface shaped to receive and secure a rod attached to a plurality of bone screws that are already inserted into vertebral bodies and that have already received the rod in a head sleeve of the inserted bone screws, and wherein the locking coupler is adapted to apply a compressive clamping force to the rod so as to fix the locking rod coupler to the rod;
   providing a sliding rod coupler adapted to be slidable on the rod and to slide against one of the inserted bone screws relative to the locking coupler secured to the rod in order to adjust a distance between two inserted bone screws, the adjustment causing one inserted bone screw to slide along the rod;
   attaching the locking rod coupler and the sliding rod coupler to a distractor which is configured to slide the sliding rod coupler relative to the locking rod coupler.

2. The method of claim 1, wherein the locking rod coupler includes:
   applying compressive clamping force to a driver disposed around the locking coupler and
   applying linear force to the driver by rotating a nut coupled to the locking coupler.

3. The method of claim 1, providing a textured surface on the mating surface of the locking rod coupler for gripping the rod.

4. The method of claim 3, wherein the locking coupler includes an angled outer surface, and wherein the driver comprises an angled inner surface, and wherein the driver radially compresses the locking coupler.

5. The method of claim 3, wherein the driver includes an attachment lug and a forcing surface that engages a corresponding shoulder on the locking coupler.

6. The method of claim 3, further comprising the distractor including:
   a first arm attached to the driver of the locking rod coupler and a second arm attached to the sliding rod coupler, wherein the first arm and the second arm are pivotally coupled.

7. The method of claim 6, wherein the distractor further includes an adjustment knob, pivoting blocks, and a screw that extends from the adjustment knob through the pivoting blocks, wherein rotation of the screw moves the pivoting blocks with respect to one another, and wherein the pivoting blocks are pivotably coupled to the first arm and the second arm.

8. The method of claim 1, wherein the locking coupler includes a split extending proximally from a distal end along a longitudinal axis to permit the driver to apply the clamping force by radially compressing the locking coupler.

9. The method of claim 1, flexing radially an extension arm of the locking coupler towards a longitudinal axis of the locking rod coupler, and wherein the extension arm includes portions of the mating surface.

10. The method of claim 9, wherein the locking coupler includes an angled shoulder between a proximate end of a distal end.

* * * * *